(12) United States Patent
Zuberi et al.

(10) Patent No.: US 9,175,212 B2
(45) Date of Patent: Nov. 3, 2015

(54) ORGANIC SEMICONDUCTORS

(75) Inventors: Tania Zuberi, Middlesex (GB); Sheena Zuberi, Middlesex (GB)

(73) Assignee: CAMBRIDGE DISPLAY TECHNOLOGY LIMITED, Cambridgeshire (GB)

( * ) Notice: Subject to any disclaimer, the term of this patent is extended or adjusted under 35 U.S.C. 154(b) by 1153 days.

(21) Appl. No.: 13/129,358

(22) PCT Filed: Nov. 27, 2009

(86) PCT No.: PCT/GB2009/002735
§ 371 (c)(1),
(2), (4) Date: Jun. 21, 2011

(87) PCT Pub. No.: WO2010/061176
PCT Pub. Date: Jun. 3, 2010

(65) Prior Publication Data
US 2011/0250719 A1    Oct. 13, 2011

(30) Foreign Application Priority Data
Nov. 28, 2008 (GB) .................................. 0821703.6

(51) Int. Cl.
| | | |
|---|---|---|
| H01L 51/30 | (2006.01) |
| H01B 1/12 | (2006.01) |
| C07D 333/50 | (2006.01) |
| C09K 11/06 | (2006.01) |
| C07D 495/22 | (2006.01) |
| H01L 51/00 | (2006.01) |
| H05B 33/10 | (2006.01) |
| H01L 51/05 | (2006.01) |

(52) U.S. Cl.
CPC ............... *C09K 11/06* (2013.01); *C07D 495/22* (2013.01); *H01L 51/0074* (2013.01); *H05B 33/10* (2013.01); *C09K 2211/1011* (2013.01); *C09K 2211/1092* (2013.01); *C09K 2211/1416* (2013.01); *C09K 2211/1425* (2013.01); *C09K 2211/1458* (2013.01); *H01L 51/0545* (2013.01)

(58) Field of Classification Search
USPC ......... 438/99; 549/41; 252/500; 257/E51.027
See application file for complete search history.

(56) References Cited

U.S. PATENT DOCUMENTS

| | | |
|---|---|---|
| 2004/0002576 A1 | 1/2004 | Oguma et al. |
| 2007/0161776 A1 | 7/2007 | He |
| 2009/0090906 A1 | 4/2009 | Chuman |
| 2010/0201259 A1 | 8/2010 | Kobayashi |

FOREIGN PATENT DOCUMENTS

| | | |
|---|---|---|
| EP | 1 028 440 A1 | 8/2000 |
| GB | 2 447 173 A | 9/2008 |
| JP | 2007-088222 A | 4/2007 |
| JP | 2008-010541 A | 1/2008 |
| WO | WO-00/53656 A1 | 9/2000 |
| WO | WO-01/78162 A2 | 10/2001 |
| WO | WO-2006/031893 A2 | 3/2006 |
| WO | WO-2007/058368 A1 | 5/2007 |
| WO | WO-2007/068618 A1 | 6/2007 |
| WO | WO-2007/116660 A1 | 10/2007 |
| WO | WO-2008/106019 A2 | 9/2008 |
| WO | WO-2008/131835 A1 | 11/2008 |
| WO | WO-2009/017056 A1 | 2/2009 |

OTHER PUBLICATIONS

Yamamoto, "Electrically Conducting and Thermally Stable π-Conjugated Poly(Arylene)s Prepared by Organometallic Processes," *Prog. Polym. Sci.*, 17:1153-1205 (1993).
International Preliminary Report on Patentability for Application No. PCT/GB2009/002735, dated May 31, 2011.
International Search Report and Written Opinion for Application No. PCT/GB2009/002735, dated May 4, 2010.
Search Report for Application No. GB0821703.6, dated May 8, 2009.

*Primary Examiner* — Kristin Vajda (57) ABSTRACT

An organic semiconducting compound comprising the structure of formula (I):

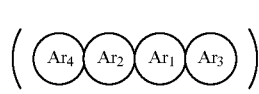

where $Ar_1$, $Ar_2$, $Ar_3$ and $Ar_4$ independently comprise monocyclic aromatic rings and at least one of $Ar_1$, $Ar_2$, $Ar_3$ and $Ar_4$ is substituted with at least one substituent X, which in each occurrence may be the same or different and is selected from the group consisting of (i) optionally substituted straight, branched or cyclic alkyl chains with 1 to 20 carbon atoms, alkoxy, amino, amido, silyl or alkenyl, or (ii) a polymerizable or reactive group selected from the group consisting of halogens, boronic acids, diboronic acids and esters of boronic acids and diboronic acids, alkylene groups and stannyl groups, and where $Ar_1$, $Ar_2$, $Ar_3$ and $Ar_4$ may each optionally be fused to one or more further rings. The organic semiconducting compound is used as an active layer in an organic semiconducting device such as a thin film transistor.

10 Claims, 5 Drawing Sheets

ORGANIC SEMICONDUCTORS

The present invention relates generally to organic semiconductor materials and in particular to organic semiconductors for forming part of a thin film transistor.

BACKGROUND OF THE INVENTION

Transistors can be divided into two main types: bipolar junction transistors and field-effect transistors. Both types share a common structure comprising three electrodes with a semiconductive material disposed there between in a channel region. The three electrodes of a bipolar junction transistor are known as the emitter, collector and base, whereas in a field-effect transistor the three electrodes are known as the source, drain and gate. Bipolar junction transistors may be described as current-operated devices as the current between the emitter and collector is controlled by the current flowing between the base and emitter. In contrast, field-effect transistors may be described as voltage-operated devices as the current flowing between source and drain is controlled by the voltage between the gate and the source.

Transistors can also be classified as p-type and n-type according to whether they comprise semiconductive material which conducts positive charge carriers (holes) or negative charge carriers (electrons) respectively. The semiconductive material may be selected according to its ability to accept, conduct, and donate charge. The ability of the semiconductive material to accept, conduct and donate holes or electrons can be enhanced by doping the material.

For example, a p-type transistor device can be formed by selecting a semiconductive material which is efficient at accepting, conducting, and donating holes, and selecting a material for the source and drain electrodes which is efficient at injecting and accepting holes from the semiconductive material. Good energy-level matching of the Fermi-level in the electrodes with the HOMO level of the semiconductive material can enhance hole injection and acceptance. In contrast, an n-type transistor device can be formed by selecting a semiconductive material which is efficient at accepting, conducting, and donating electrons, and selecting a material for the source and drain electrodes which is efficient at injecting electrons into, and accepting electrons from, the semiconductive material. Good energy-level matching of the Fermi-level in the electrodes with the LUMO level of the semiconductive material can enhance electron injection and acceptance.

Transistors can be formed by depositing the components in thin films to form a thin film transistor (TFT). When an organic material is used as the semiconductive material in such a device, it is known as an organic thin film transistor (OTFT).

OTFTs may be manufactured by low cost, low temperature methods such as solution processing. Moreover, OTFTs are compatible with flexible plastic substrates, offering the prospect of large-scale manufacture of OTFTs on flexible substrates in a roll-to-roll process.

Figure 4:
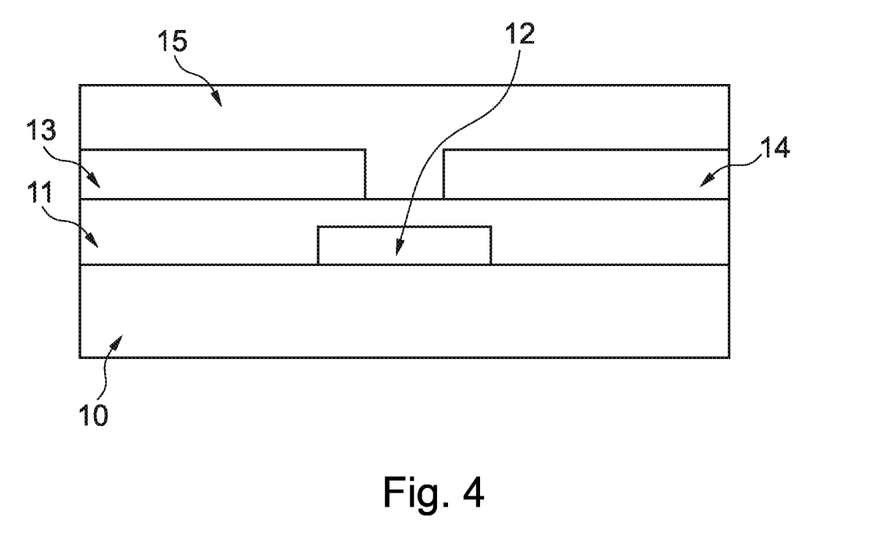
FIG. 4 is a schematic diagram of a general architecture of a bottom-gate organic thin film transistor according to the prior art.

With reference to FIG. 4, the general architecture of a bottom-gate organic thin film transistor (OTFT) comprises a gate electrode 12 deposited on a substrate 10. An insulating layer 11 of dielectric material is deposited over the gate electrode 12 and source and drain electrodes 13, 14 are deposited over the insulating layer 11 of dielectric material. The source and drain electrodes 13, 14 are spaced apart to define a channel region therebetween located over the gate electrode 12. An organic semiconductor (OSC) material 15 is deposited in the channel region for connecting the source and drain electrodes 13, 14. The OSC material 15 may extend at least partially over the source and drain electrodes 13, 14.

Alternatively, it is known to provide a gate electrode at the top of an organic thin film transistor to form a so-called top-gate organic thin film transistor. In such an architecture, source and drain electrodes are deposited on a substrate and spaced apart to define a channel region there between. A layer of an organic semiconductor material is deposited in the channel region to connect the source and drain electrodes and may extend at least partially over the source and drain electrodes. An insulating layer of dielectric material is deposited over the organic semiconductor material and may also extend at least partially over the source and drain electrodes. A gate electrode is deposited over the insulating layer and located over the channel region.

An organic thin film transistor can be fabricated on a rigid or flexible substrate. Rigid substrates may be selected from glass or silicon and flexible substrates may comprise thin glass or plastics such as poly(ethylene-terephthalate) (PET), poly(ethylene-naphthalate) (PEN), polycarbonate and polyimide.

The organic semiconductive material may be made solution processable through the use of a suitable solvent. Exemplary solvents include mono- or poly-alkylbenzenes such as toluene and xylene; tetralin; and chloroform. Preferred solution deposition techniques include spin coating and ink jet printing. Other solution deposition techniques include dip-coating, roll printing and screen printing.

The length of the channel defined between the source and drain electrodes may be up to 500 microns, but preferably the length is less than 200 microns, more preferably less than 100 microns, most preferably less than 20 microns.

The gate electrode can be selected from a wide range of conducting materials for example a metal (e.g. gold) or metal compound (e.g. indium tin oxide). Alternatively, conductive polymers may be deposited as the gate electrode. Such conductive polymers may be deposited from solution using, for example, spin coating or ink jet printing techniques and other solution deposition techniques discussed above.

The insulating layer comprises a dielectric material selected from insulating materials having a high resistivity. The dielectric constant, k, of the dielectric is typically around 2-3 although materials with a high value of k are desirable because the capacitance that is achievable for an OTFT is directly proportional to k, and the drain current ID is directly proportional to the capacitance. Thus, in order to achieve high drain currents with low operational voltages, OTFTs with thin dielectric layers in the channel region are preferred.

The dielectric material may be organic or inorganic. Preferred inorganic materials include $SiO_2$, $SiN_x$ and spin-on-glass (SOG). Preferred organic materials are generally polymers and include insulating polymers such as poly vinylalcohol (PVA), polyvinylpyrrolidine (PVP), acrylates such as polymethylmethacrylate (PMMA), fluorinated polymers and benzocyclobutanes (BCBs) available from Dow Corning. The insulating layer may be formed from a blend of materials or comprise a multi-layered structure.

The dielectric material may be deposited by thermal evaporation, vacuum processing or lamination techniques as are known in the art. Alternatively, the dielectric material may be deposited from solution using, for example, spin coating or ink jet printing techniques and other solution deposition techniques discussed above.

If the dielectric material is deposited from solution onto the organic semiconductor, it should not result in dissolution of the organic semiconductor. Likewise, the dielectric material should not be dissolved if the organic semiconductor is deposited onto it from solution. Techniques to avoid such dissolution include: use of orthogonal solvents for example use of a solvent for deposition of the uppermost layer that does not dissolve the underlying layer; and cross linking of the underlying layer.

The thickness of the insulating layer is preferably less than 2 micrometers, more preferably less than 500 nm.

Organic semiconductors are a class of organic molecules having extensively conjugated pi systems allowing for the movement of electrons.

Preferred methods for preparation of these molecules are Suzuki reactions (coupling or polymerization reactions) as described in, for example, WO 2000/53656 and Yamamoto polymerization as described in, for example, T. Yamamoto, "Electrically Conducting And Thermally Stable pi-Conjugated Poly(arylene)s Prepared by Organometallic Processes", Progress in Polymer Science 1993, 17, 1153-1205. These techniques both operate via a "metal insertion" wherein the metal atom of a metal complex catalyst is inserted between an aryl group and a leaving group of a monomer. In the case of Yamamoto polymerization, a nickel complex catalyst is used; in the case of Suzuki reaction, a palladium complex catalyst is used.

For example, in the synthesis of a linear polymer by Yamamoto polymerization, a monomer having two reactive halogen groups is used. Similarly, according to the method of Suzuki reaction, at least one reactive group is a boron derivative group such as a boronic acid or boronic ester and the other reactive group is a halogen. Preferred halogens are chlorine, bromine and iodine, most preferably bromine.

Alternatively, stannyl groups may be used as reactive groups in polymerization or coupling reactions (Stille reactions).

The performance of organic semiconductors is typically assessed by measurement of its "charge mobility" (cm$^2$ V$^{-1}$ s$^{-1}$), which may relate to either the mobility of holes or electrons. This measurement relates to the drift velocity of charge carriers to an applied electric field across a material.

Organic semiconductors having relatively high mobilities tend to be those which comprise compounds having a rigid planar structure with extensive conjugation which allows for efficient and effective pi-pi stacking in the solid state.

WO 2007/068618 describes a variety of organic semiconductors, each comprising an array of fused aromatic rings having a central benzene ring substituted with acetylene groups.

JP 2007/088222 and WO 2007/116660 describe the use of benzodithiophenes and its derivatives in small molecule, oligomeric and polymeric form, as organic semiconductors.

However, the increased level of conjugation required to allow compounds to form such a pi-pi stack may also result in a decrease in band gap and stability of the semiconductor, leading to poor performance and a short lifetime. Moreover, these compounds may be highly insoluble due to the size of molecule required to achieve extended conjugation, which poses particular problems in synthesis and renders their use in efficient transistor production methods, such as ink-jet printing, difficult.

SUMMARY OF THE INVENTION

The present invention seeks to provide an organic semiconductor having high mobility, good solubility and good stability (in particular stability in the ambient environment such as stability to oxidation).

In a first aspect, the present invention relates to an organic semiconducting device comprising an organic semiconducting compound of formula (I):

I where $Ar_1$, $Ar_2$, $Ar_3$ and $Ar_4$ independently comprise monocyclic aromatic rings and at least one of $Ar_1$, $Ar_2$, $Ar_3$ and $Ar_4$ is substituted with at least one substituent X, which in each occurrence may be the same or different and is selected from the group consisting of (i) optionally substituted straight, branched or cyclic alkyl chains with 1 to 20 carbon atoms, alkoxy, amino, amido, silyl or alkenyl, or (ii) a polymerisable or reactive group selected from the group consisting of halogens, boronic acids, diboronic acids and esters of boronic acids and diboronic acids, alkylene groups and stannyl groups, and where $Ar_1$, $Ar_2$, $Ar_3$ and $Ar_4$ may each optionally be fused to one or more further rings.

The groups $Ar_1$, $Ar_2$, $Ar_3$ and $Ar_4$ may be carbocyclic or heterocyclic aromatics. Preferably $Ar_1$, $Ar_2$, $Ar_3$ and $Ar_4$ are independently benzene or thiophene.

Preferably, a plurality of substituents X is provided. It is preferred that at least one non-terminal ring ($Ar_1$ or $Ar_2$) is substituted. In one preferred embodiment, at least two substituents X are provided on the same aromatic ring, preferably $Ar_1$.

The strategically positioned substituent groups X described above provide enhanced solubility, allowing the compound to be solution processed. Moreover, these substituent groups allow the mesogenic region of the compound to self-align into regioregular structures of close-packed lamellar sheets.

Preferred substituent groups for solubilisation are alkyl groups, preferably $C_4$-$C_{18}$ alkyl, most preferably octy, decyl and hexydecyl.

Meanwhile, the large, rigid coplanar structures provided by compounds of the invention give extended pi-conjugation and increased inter- and intra-molecular mobility.

Preferably, some or all of $Ar_2$ to $Ar_4$ comprise heterocyclic aromatic groups.

The compound of formula (I) may be fused to one or more further aryl groups. Thus, in one preferred embodiment, a further aryl group $Ar_5$ is fused with $Ar_3$ to provide a structure:

II

The further aryl group $Ar^5$ may comprise a heterocyclic aromatic group. In this case, substituents X are preferably provided at least on one or more of the non-terminal aryl groups $Ar_1$, $Ar_2$ and $Ar_3$.

Each of $Ar_4$ and $Ar_5$ is optionally substituted.

In certain embodiments, $Ar_4$ may be fused to a further aryl system $Ar_6$ to provide a structure:

III which aryl system Ar$_6$ is optionally substituted and may comprise a heterocyclic aromatic group.

In this case, substituents X are preferably provided on one or more of the non-terminal aryl groups Ar$_1$, Ar$_2$, Ar$_3$ and Ar$_4$.

In some embodiments, Ar$_5$ is fused to a further aryl system Ar$_7$ to provide a structure:

IV where the aryl system Ar$_7$ is optionally substituted and may comprise a heterocyclic aromatic group.

In this case, substituents X are preferably provided on one or more of the non-terminal aryl groups Ar$_1$, Ar$_2$, Ar$_3$, Ar$_4$ and Ar$_5$.

The above structures illustrate compounds having from 4 to 7 fused rings, however it will be appreciated that yet further rings may be fused to these compounds to form compounds having conjugation extending across 8 or more fused rings.

Preferably, structure II comprises:

where Z$_1$ and Z$_2$ are independently S, O, Se or NR; W$_1$ and W$_2$ are independently S, O, Se, NR or —CR═CR—; R is H or a substituent group; and X$_1$ and X$_2$, which may be the same or different, are selected from substituents X.

Preferably, the structure IV comprises the structure:

where V$_1$ and V$_2$ are independently S, O, Se, NR, NR or —CR═CR—.

More preferably, the structure IV comprises the structure:

Preferably, one or both of the terminal aryl groups of structures I to IV is substituted with one or more substituent groups X one of which groups comprises a reactive or polymerisable group or optionally substituted straight, branched or cyclic alkyl chains having 1 to 20 carbon atoms, alkoxy, amino, amido, silyl, alkyl or alkenyl, the remaining groups independently comprising hydrogen or optionally substituted straight, branched or cyclic alkyl chains having 1 to 20 carbon atoms, alkoxy, amino, amido, silyl, alkyl or alkenyl.

The reactive or polymerisable groups preferably independently comprise such moieties as halogens; boronic acids, diboronic acids and esters of boronic acids and diboronic acids; alkylene groups; and stannyl groups.

The terminal aryl groups represent aryl groups fused to just one other aryl group, for example, structure III has terminal aryl groups Ar$_4$ and Ar$_3$, while structure IV has terminal aryl groups Ar$_6$ and Ar$_7$. For instance, structure IV may comprise the structure:

wherein X$_1$-X$_{10}$, which may be the same or different, are selected from substituents X described above.

In some embodiments, the compound comprises a small molecule comprising any of structures I to IV. In other embodiments, the compound may comprise an oligomer or a polymer having a repeat unit comprising any of structures I to IV.

In one embodiment, the organic semiconducting device is a thin film transistor.

In a second aspect, the invention relates to an optical device comprising a thin film transistor as described herein. In one embodiment of the second aspect the optical device is an organic electroluminescent device. In another embodiment the optical device is a photo responsive device such as a photovoltaic device or a photo sensor.

In a third aspect, the invention provides an organic semiconducting compound comprising one or more of the structures I to IV.

In a further aspect, the present invention relates to a solution for forming a thin film transistor, the solution having a solute comprising a compound comprising one or more of structures I to IV and a solvent. Preferably, the solvent is selected from the group comprising substituted benzenes, preferably benzene substituted with one or more substituents selected from halogen and alkyl, for example tetralin, n-butylbenzene, toluene, chlorobenzene and 1,3,5-trimethylbenzene.

Preferably, the concentration of the compound of formula (I) is more than 0.5% weight per volume, preferably 1.0% w/v and most preferably 2.0% w/v. This concentration may be achieved by the provision of solubilising groups X.

In a further aspect, the invention relates to a method for forming a transistor comprising applying a solution having a solute comprising a compound comprising any of structures I to IV onto a substrate. Preferably, the solution is applied by ink-jet printing.

In a further aspect, the invention relates to a method for synthesizing a semiconductive compound, the method comprising fusing one or more further aryl groups to a compound comprising the structure:

where $Z_1$ and $Z_2$ are independently S, O, Se or NR, where R is H or a substituent group, and $X_1$ and $X_2$ independently comprise one of (i) optionally substituted straight, branched or cyclic alkyl chains with 1 to 20 carbon atoms, alkoxy, amino, amido, silyl or alkenyl, wherein 2 or more substituents X may be linked to form a ring or (ii) a polymerisable or reactive group selected from the group consisting of halogens, boronic acids, diboronic acids and esters of boronic acids and diboronic acids, alkylene groups and stannyl groups; and wherein the one or more of the further aryl groups may be heterocyclic.

Preferably, structures I-IV are synthesized by means of a Suzuki reaction—this is desirable because it avoids the problems of metallic catalyst residues and delicate reaction conditions associated with other methods—followed by an acid induced intramolecular cyclization reaction.

Exemplary compounds according to the present invention include the following:

M = N, O, S wherein $X_{11}$—$X_{13}$, which may be the same or different, are selected from substituents X described above.

Polymerization of these compounds, if desired, may be performed using techniques such as Suzuki, Stillie or Yamamoto polymerization. Exemplary polymers formed by such polymerization are as follows:

BRIEF DESCRIPTION OF THE FIGURES

Embodiments of the invention will now be described, by way of example only, and with reference to the accompanying drawings in which.

DETAILED DESCRIPTION

Throughout the following description like reference numerals shall be used to identify like parts.

Figure 1:
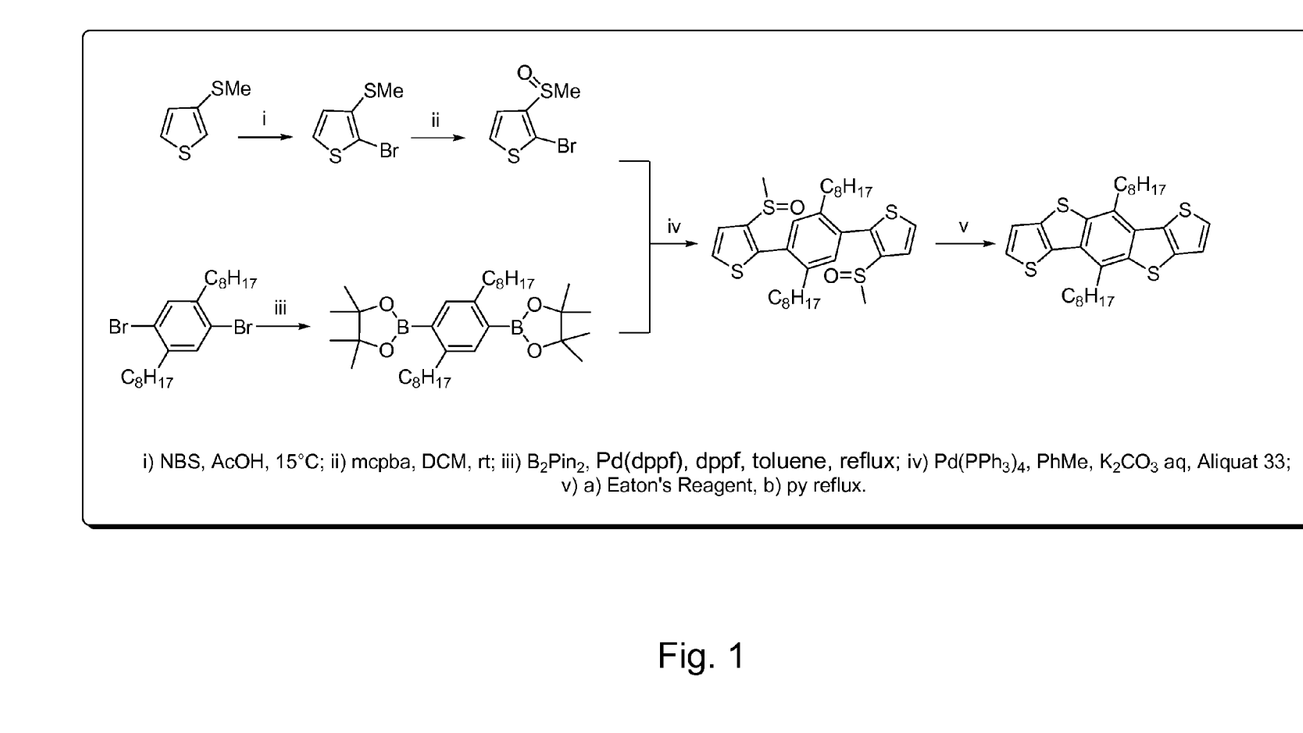
FIG. 1 shows a synthesis of a compound according to the invention, as also described in Intermediates 1 to 4 and Example 1.

Organic semiconductors according to the present invention may be manufactured by means of a Suzuki coupling reaction followed by an acid induced intramolecular cyclization reaction as described below [FIG. 1].

Intermediate 1

A solution of 3-bromothiophene (100 g, 0.61 mol) in diethyl ether (750 ml) under nitrogen was cooled to −78° C. and n-butyllithium (294.4 ml, 0.74 mmol, 2.5M in hexanes) added drop wise. After stirring for a further 20 minutes at this temperature, the mixture was transferred via cannula to an ice cool solution of methyldisulfide (144.3 g, 1.53 mmol) in diethyl ether (550 ml); the reaction mixture was warmed to room temperature and stirred at this temperature for a further 12 hrs. Water (500 ml) was added and the organic layer separated, washed with water, dried (MgSO$_4$) and concentrated under reduced pressure. Distillation of the crude product gave Intermediate 1 as a yellow oil (43.1 g, 54%, 70° C., 15 mmHg).

Intermediate 2

To a stirred solution of Intermediate 1 (42 g, 0.32 mol) in acetic acid (200 ml) at 15° C., was added N-bromosuccinimide (57.4 g, 0.32 mol) portion wise at such a rate so as to maintain the temperature between 15° C. and 17° C. The resulting mixture was allowed to warm to room temperature overnight, poured into water and extracted with dichloromethane. The organic phase was washed with water, saturated aqueous NaHCO$_3$, dried (MgSO$_4$) and concentrated under reduced pressure. Purification by column chromatography (silica gel, hexane) gave Intermediate 2 as colorless oil (32 g, 48%).

Intermediate 3

To a solution of Intermediate 2 (18 g, 86.1 mmol) in dichloromethane (360 ml) at 0° C., was added 3-chloro-perbenzoic acid (31.2 g, 90.4 mmol, 50-55%) portion wise and the resulting solution allowed to stir at room temperature for 12 hrs. The reaction mixture was washed with aqueous Na$_2$CO$_3$, dried (MgSO$_4$) and concentrated under reduced pressure to give Intermediate 3 as an yellow oil (15.2 g, 78%). This was used without any further purification. $^1$H NMR (CDCl$_3$, 400 MHz) $\delta_{ppm}$ 7.44 (1H, d, J=6.3 Hz), 7.36 (1H, d, J=6.3 Hz), 2.80 (3H, s).

Intermediate 4

A solution of Intermediate 3 (11.2 g, 49.75 mmol) and 2,5-dioctylphenylene-1,4-bis(4,4,5,5-tetramethyl-1,3,2-dioxaborolate)(12 g, 21.66 mmol) in toluene was degassed with nitrogen for 1 hr. Pd(PPh$_3$)$_4$ (1.25 g, 0.05 mol %) was added followed by a solution of K$_2$CO$_3$ (10%, 8.97 g, 64.90 mmol) and a few drops of Aliquat 336 after a further 5 mins and the mixture allowed to stir at reflux for 24 hrs. The mixture was diluted with toluene, the aqueous phase separated, and the organics filtered through celite, washed with water, dried (MgSO$_4$) and concentrated under reduced pressure. Purification by column chromatography (silca gel, 10% methanol/dichloromethane) gave intermediate 4 as a beige solid (10.3 g, HPLC 82%) which was used without further purification. $^1$H NMR (CDCl$_3$, 400 MHz) $\delta_{ppm}$ 7.60 (2H, d, J=5.9 Hz), 7.53 (2H, d, J=5.9 Hz), 7.14 (2H, s), 2.70 (6H, s), 2.52 (4H, m), 1.48 (4H, m), 1.20 (20H, m), 0.85 (6H, t, J=7.4 Hz).

EXAMPLE 1

A solution of Intermediate 4 (1 g, 1.69 mmol) in Eaton's Reagent (7 ml) was stirred at room temperature in the dark for 48 hrs. The dark green solution was poured into ice-water (100 ml) and the resulting sticky brown solid dissolved in pyridine (60 ml) and the solution stirred at reflux for 18 hrs. The mixture was cooled, poured into dichloromethane (600 ml) and washed thoroughly with 2M HCl and water, it was then dried (MgSO$_4$) and concentrated under reduced pressure. Purification by column chromatography (silica gel, 5% dichloromethane:hexane) gave Example 1 as a white solid (240 mg, 35%, HPLC 99.6%); mp (DSC) 126.5° C.; $^1$H NMR (CDCl3, 400 MHz) $\delta_{ppm}$ 7.57 (2H, d, J=4.8 Hz), 7.37 (2H, d, J=4.8 Hz), 3.27 (4H, t, J=8 Hz), 1.85 (4H, m), 1.61 (4H, m), 1.40 (4H, m), 1.30 (12H, m), 0.88 (6H, t, J=7.4 Hz).

EXAMPLE 2

Example 2 was synthesized in a similar manner to that described for Example 1 by means of a Suzuki coupling reaction followed by an acid induced intramolecular cyclization reaction.

EXAMPLE 3

Figure 2:
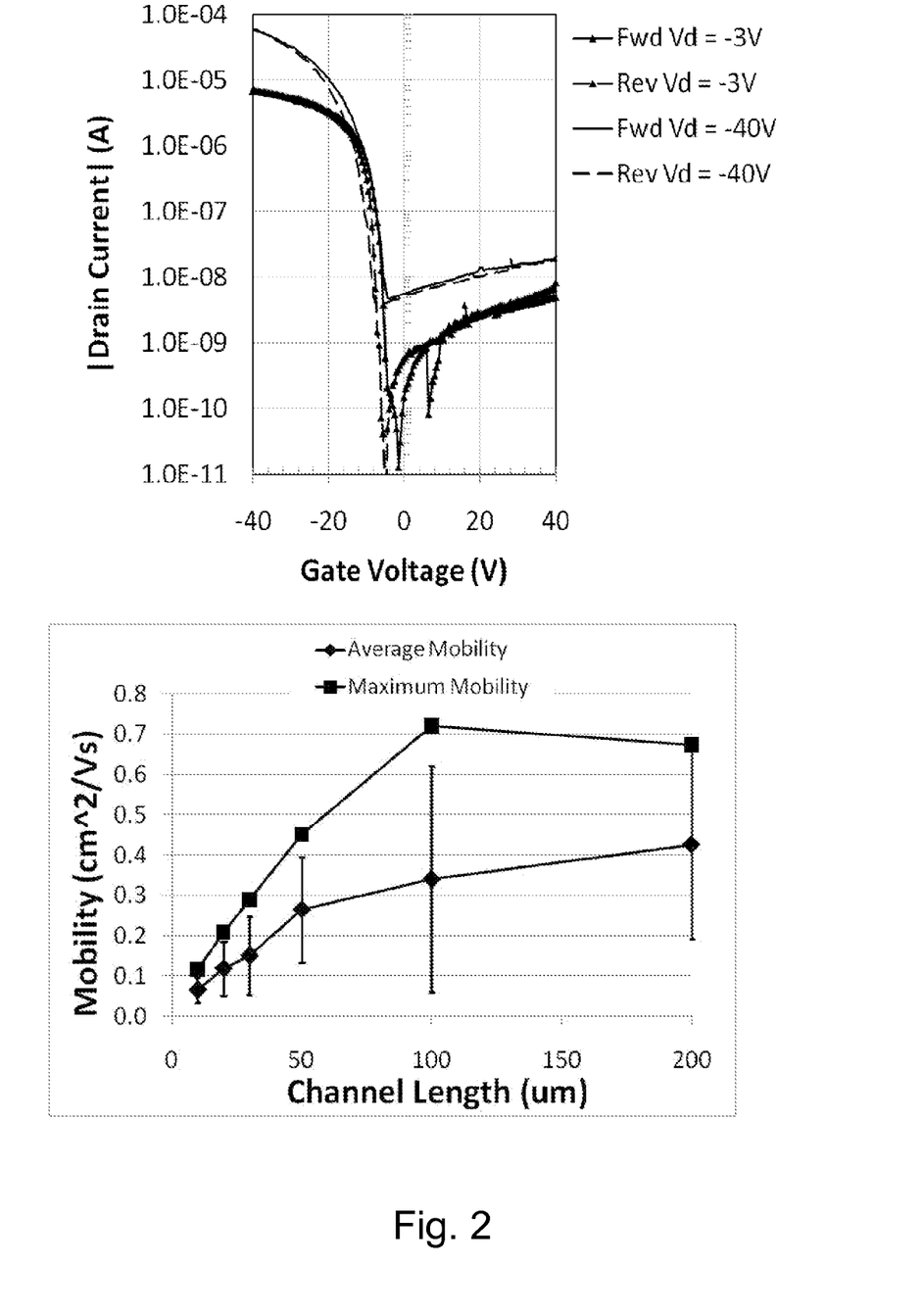
FIG. 2 shows performance data for an organic field effect transistor device of Example 3, which includes the semiconductor synthesizing in Example 1.

Organic field effect transistor devices using compound of Example 1 as the active layer were fabricated in a top gate, bottom contact device. Gold source drain contacts were defined by lift off on a glass substrate. Channel lengths of 10-200 μm and widths of 2 mm were defined. Devices were fabricated by spin-coating the compound of example 1, onto the cleaned substrates from a 2% tetralin solution at 1000 rpm for 60 seconds. The film was subsequently dried on a hotplate at 80° C. for 10 mins and cooled on a metal block for 1 minute. A fluorinated dielectric material was spin-coated from a fluorosolvent on to the semiconductor layer, dried on a hotplate at 80° C. for 10 mins and cooled on a metal block for 1 min. The highest mobility in saturation observed was 0.71 cm$^2$/Vs at 100 μm channel length. An on/off ratio of ~10$^4$ was obtained. A contact resistance of 27 kOhm-cm was calculated by the extrapolation method at −40V Vg or a gate field of 16V/100 nm [FIG. 2].

EXAMPLE 4

Figure 3:
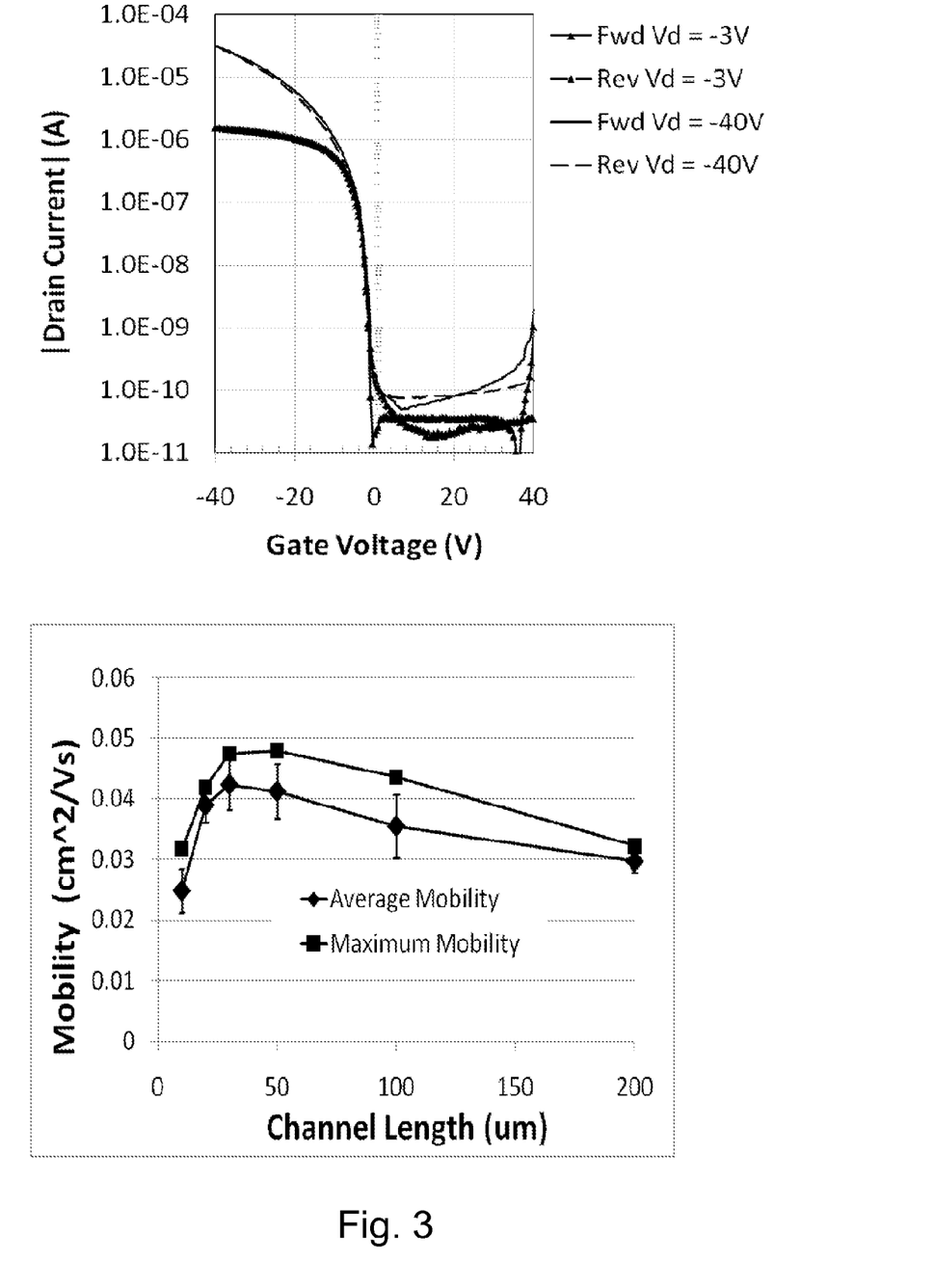
FIG. 3 shows performance data for an organic field effect transistor device of Example 3, which includes the semiconductor synthesizing in Example 1.

Organic field effect transistor devices using compound of Example 2 as the active layer were fabricated in a top gate, bottom contact device. Gold source drain contacts were defined by lift off on a glass substrate. Channel lengths of 10-200 μm and widths of 2 mm were defined. Devices were fabricated by spin-coating the compound of example 2, onto the cleaned substrates, from a 2% 1,3,5-trimethylbenzene solution at 1000 rpm for 60 secs, the semiconductor solution, substrate and spin coater chuck were all raised to elevated temperatures (80° C.) immediately prior to the spin coating step of the material. The film was subsequently dried on a hotplate at 80° C. for 5 mins and cooled on a metal block for 1 min. A fluorinated dielectric material was spin-coated from a fluorosolvent on to the semiconductor layer, dried on a hotplate at 80° C. for 10 mins and cooled on a metal block for 1 min. The highest mobility in saturation observed was 0.05 cm$^2$/Vs at 50 μm channel length. An on/off ratio of 10$^{-5}$ was obtained. A contact resistance of 180 kOhm-cm was calculated by the extrapolation method at −40V Vg or a gate field of 16V/100 nm [FIG. 3].

The resulting compounds are easily soluble and may thus be applied by ink-jet printing onto a substrate to provide the semiconducting layer 15 in a thin film transistor such as is shown in FIG. 4.

An application of such an organic thin film transistor (OTFT) may be to drive pixels in an optical device, preferably an organic optical device. Examples of such optical devices include photoresponsive devices, in particular photodetectors, and light-emissive devices, in particular organic light emitting devices. OTFTs are particularly suited for use with active matrix organic light emitting devices, e.g. for use in display applications.

Figure 5:
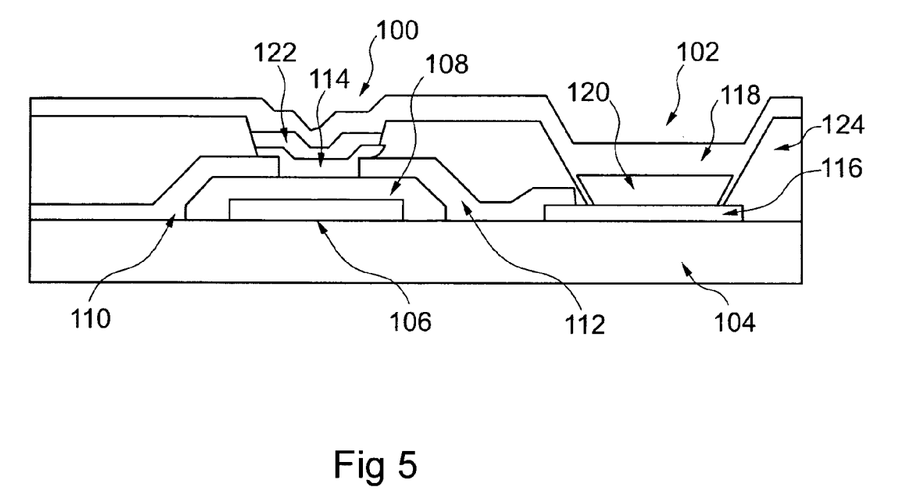
FIG. 5 is a schematic diagram of a pixel comprising an organic thin film transistor and an adjacent organic light emitting device fabricated on a common substrate according to an embodiment of the present invention.

FIG. 5 shows a pixel comprising an organic thin film transistor 100 and an adjacent organic light emitting device (OLED) 102 fabricated on a common substrate 104. The OTFT 100 comprises gate electrode 106, dielectric layer 108, source and drain electrodes 110 and 112 respectively, and OSC layer 114. The OLED 102 comprises anode 116, cathode 118 and an electroluminescent layer 120 provided between the anode 116 and cathode 118. Further layers may be located between the anode 116 and cathode 118, such as charge transporting, charge injecting or charge blocking layers. In the embodiment of FIG. 5, the layer of cathode material 118 extends across both the OTFT 100 and the OLED 102, and an insulating layer 122 is provided to electrically isolate the cathode layer 118 from the OSC layer 114. The active areas of the OTFT 100 and the OLED 102 are defined by a common bank material formed by depositing a layer of photoresist 124 on substrate 104 and patterning it to define OTFT 100 and OLED 102 areas on the substrate.

In FIG. 5, the drain electrode 112 is directly connected to the anode 116 of the organic light emitting device 102 for switching the organic light emitting device 102 between emitting and non-emitting states.

Figure 6:
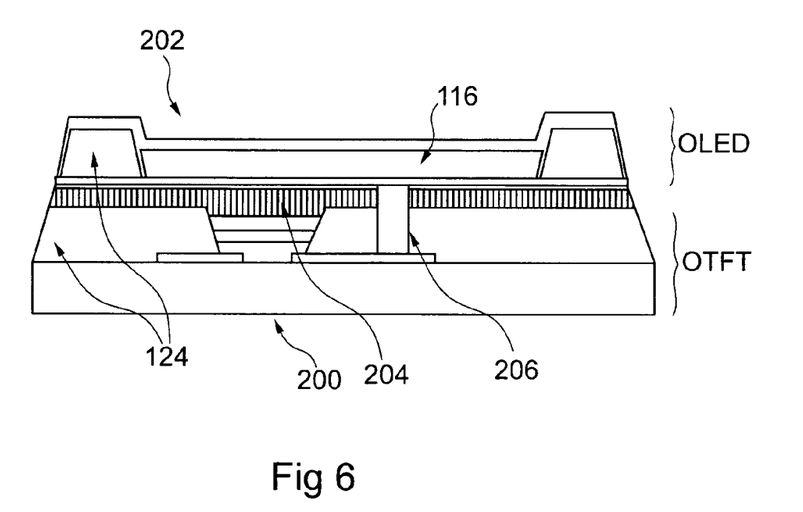
FIG. 6 is a schematic diagram of an organic thin film transistor fabricated in a stacked relationship to an organic light emitting device according to an embodiment of the present invention.

In an alternative arrangement illustrated in FIG. 6, an organic thin film transistor 200 may be fabricated in a stacked relationship to an organic light emitting device 202. In such an embodiment, the organic thin film transistor 202 is built up as described above in either a top or bottom gate configuration. As with the embodiment of FIG. 5, the active areas of the OTFT 200 and OLED 202 are defined by a patterned layer of photoresist 124, however in this stacked arrangement, there are two separate bank layers 124—one for the OLED 202 and one for the OTFT 200. A planarization layer 204 (also acting as a passivation layer) is deposited over the OTFT 200. Exemplary passivation layers 204 include BCBs and parylenes. The organic light emitting device 202 is fabricated over the passivation layer 204 and the anode 116 of the organic light emitting device 202 is electrically connected to the drain electrode 112 of the OTFT 200 by a conductive via 206 passing through passivation layer 204 and bank layer 124.

It will be appreciated that pixel circuits comprising an OTFT and an optically active area (e.g. light emitting or light sensing area) may comprise further elements. In particular, the OLED pixel circuits of FIGS. 5 and 6 will typically comprise least one further transistor in addition to the driving transistor shown, and at least one capacitor. It will be appreciated that the organic light emitting devices described herein may be top or bottom-emitting devices. That is, the devices may emit light through either the anode or cathode side of the device. In a transparent device, both the anode and cathode are transparent. It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminum.

Transparent cathodes are particularly advantageous for active matrix devices because emission through a transparent anode in such devices may be at least partially blocked by OTFT drive circuitry located underneath the emissive pixels as can be seen from the embodiment illustrated in FIG. 6.

Thicknesses of the gate electrode, source and drain electrodes may be in the region of 5-200 nm, although typically 50 nm as measured by Atomic Force Microscopy (AFM), for example.

Other layers may be included in the device architecture. For example, in addition to providing a self assembled monolayer (SAM) on the gate, source or drain electrodes one may be provided on the, substrate, insulating layer and organic semiconductor material to promote crystallinity, reduce contact resistance, repair surface characteristics and promote adhesion where required. In particular, the dielectric surface in the channel region may be provided with a monolayer comprising a binding region and an organic region to improve device performance, e.g. by improving the organic semiconductor's morphology (in particular polymer alignment and crystallinity) and covering charge traps, in particular for a high k dielectric surface. Exemplary materials for such a monolayer include chloro- or alkoxy-silanes with long alkyl chains, e.g. octadecyltrichlorosilane.

No doubt many other effective alternatives will occur to the skilled person. It will be understood that the invention is not limited to the described embodiments and encompasses modifications apparent to those skilled in the art lying within the scope of the following claims.

The invention claimed is:

1. An organic semiconducting device comprising an organic semiconducting compound, wherein the semiconducting compound has the structure:

where $X_1$ and $X_2$ may be the same or different and are selected from the group consisting of (i) optionally substituted straight, branched or cyclic alkyl chains with 1 to 20 carbon atoms, alkoxy amino, amido, and alkenyl, or (ii) a polymerizable or reactive group selected from the group consisting of halogens, boronic acids, diboronic acids and esters of boronic acids and diboronic acids, alkylene groups and stannyl groups; and wherein $Z_1$ and $Z_2$ are independently S, O, Se or $NR_1$, and where $W_1$ and $W_2$ are independently S, O, Se, $NR_1$ or $-CR_1=CR_1-$, where $R_1$ is H or a substituent group.

2. A thin film transistor comprising a device according to claim 1.

3. An optical device comprising a thin film transistor according to claim 2.

4. An electroluminescent device comprising a thin film transistor according to claim 2.

5. A solution for forming a thin film transistor, the solution comprising a solute comprising an organic semiconducting compound wherein the semiconducting compound has the structure:

where $X_1$ and $X_2$ may be the same or different and are selected from the group consisting of (i) optionally substituted straight, branched or cyclic alkyl chains with 1 to 20 carbon atoms, alkoxy amino, amido, and alkenyl, or (ii) a polymerizable or reactive group selected from the group consisting of halogens, boronic acids, diboronic acids and esters of boronic acids and diboronic acids, alkylene groups and stannyl groups; and wherein $Z_1$ and $Z_2$ are independently S, O, Se or $NR_1$, and where $W_1$ and $W_2$ are independently S, O, Se, $NR_1$ or $-CR_1=CR_1-$, where $R_1$ is H or a substituent group.

6. A solution according to claim 5 comprising a solvent selected from the group consisting of substituted benzenes.

7. A method for forming a transistor comprising applying a solution according to claim 5 to a substrate.

8. A method according to claim 7 comprising applying the solution by ink-jet printing.

9. A semiconductive compound comprising a structure selected from the group consisting of:

where $X_1$, $X_2$, $X_4$, $X_5$, $X_8$ and $X_9$ may be the same or different and are selected from the group consisting of (i) optionally substituted straight, branched or cyclic alkyl chains with 1 to 20 carbon atoms, alkoxy amino, amido, and alkenyl, or (ii) a polymerizable or reactive group selected from the group consisting of halogens, boronic acids, diboronic acids and esters of boronic acids and diboronic acids, alkylene groups and stannyl groups; and wherein $Z_1$ and $Z_2$ are independently S, O, Se or $NR_1$, and where $W_1$ and $W_2$ are independently S, O, Se, $NR_1$ or —$CR_1$=$CR_1$—, where $R_1$ is H or a substituent group.

10. A solution according to claim 6 comprising a solvent selected from the group consisting of benzenes substituted with one or more substituents selected from halogen and alkyl.

* * * * *